United States Patent [19]
Takagi et al.

[11] Patent Number: 5,539,796
[45] Date of Patent: Jul. 23, 1996

[54] SPIRAL SCANNING TYPE X-RAY CT APPARATUS

[75] Inventors: Hiroshi Takagi, Kashiwa; Kenji Hatano, Tokyo; Takashi Tsukizu, Kashiwa, all of Japan

[73] Assignee: Hitachi Medical Corporation, Tokyo, Japan

[21] Appl. No.: 177,722

[22] Filed: Jan. 5, 1994

[30] Foreign Application Priority Data

Jan. 11, 1993 [JP] Japan ................... 5-002815

[51] Int. Cl.⁶ .................................................. H05G 1/60
[52] U.S. Cl. .................................... 378/20; 378/4
[58] Field of Search ............................... 378/20, 4

[56] References Cited

U.S. PATENT DOCUMENTS 5,224,135  6/1993  Toki ......................................... 378/15

Primary Examiner—Craig E. Church
Attorney, Agent, or Firm—Antonelli, Terry, Stout & Kraus

[57] ABSTRACT

When CT imaging is effected by spiral scanning, an operator is required to set only one or two of three imaging conditions to be set, that is, a bed moving speed, a slice width of irradiation X-ray beams and an image reconstruction pitch. The CT apparatus according to the present invention determines in advance the relationship between these three imaging conditions so that when one or two of these imaging conditions are inputted, the remaining imaging condition or conditions are specified in the light of this relationship.

15 Claims, 3 Drawing Sheets

SPIRAL SCANNING TYPE X-RAY CT APPARATUS

BACKGROUND OF THE INVENTION

This invention relates to a spiral scanning type X-ray CT apparatus.

The spiral scanning type X-ray CT apparatus is known in the art as described, for example, in U.S. Pat. No. 4,789,929.

FIG. 2 of the accompanying drawings illustrates a schematic construction of the spiral scanning type X-ray CT apparatus according to the prior art. A CT scanner 3 is a spiral scanning type scanner and comprises a bed for supporting a subject, a gantry for allowing this bed to be loaded and pulled out and an X-ray source (inclusive of members such as a collimator, etc.) rotating around the gantry so that the X-ray source can be revolved while moving the bed, and the subject can be scanned spirally.

A CT controller 2 executes processing and control. The term "control" hereby means the control of movement and rotation of the CT scanner 3 and the timing control of X-ray irradiation. The term "processing" means input and storage processing of spiral data measured by the CT scanner 3, reconstruction processing of the spiral data and display processing of the reconstructed image on a display 4.

According to the CT apparatus of the prior art described above, an operator of the apparatus must input three imaging conditions, that is, the moving speed of the bed, the irradiation slice width of the X-ray beams and the pitch of the image, from an input unit 1.

In a non-spiral scanning type X-ray CT apparatus wherein the bed is kept in a halted condition halt at the time of imaging, the irradiation slice width and the image pitch are set as the imaging condition.

Here, let's take the example of mass screening with the X-ray CT apparatus. This mass screening is directed to sequentially apply CT scan to a large number of people (subjects) and to discover diseases in early stages. In other words, quick measurement of a large number of subjects by CT scan and appropriate diagnosis from the measurement result become necessary.

In such mass screening, a spiral scan capable of effecting a CT scan with a small exposure of the whole body of people is suitable for use. For, in the case of a spiral scan, the whole body is moved inside the gantry and while the X-ray source is rotated by 180°, 360° and further, 720°, during this movement, the X-ray beams are exposed. Interpolation processing, etc., is applied to the spiral data obtained by this spiral scan, and a reconstructed image for each slice vertical to the body axis (that is, a tomogram ) is obtained.

However, when the X-ray beams of 180°, 360° and further, 720°, are exposed in the same measuring condition to the whole body, the reconstructed images thus obtained does not fully meet the diagnostic purpose, therefore a spiral scan is generally carried out for each diagnostic portion of the body. The term "diagnostic portion" of the body means each characterizing portion of the body such as the head, the chest (lung), the liver, and so forth. Furthermore, depending upon the object of diagnosis, zones in the direction of the body axis of spiral scan are also different. In any case, a spiral scan capable of obtaining the tomograms of a greater number of slice portions with smaller exposure than the conventional stationary bed type CT scan, in which the X-ray source is rotated 180° or 360° while the bed is fixed, is much more preferred in the mass screening.

When a spiral scan is effected for each diagnostic portion of the body, the moving speed of the bed is mostly changed for each diagnostic portion so as to improve measurement efficiency and reliability. When the chest is diagnosed, for example, the bed is moved at a high speed while the bed is moved at a low speed to diagnose the head. On the other hand, the number of tomograms to be obtained becomes the problem depending on the diagnostic portions. When more precise diagnosis is necessary, a greater number of tomograms are required. The number of necessary tomograms varies, too, depending on the size of the width as viewed from the direction of the body axis of spiral scan. The number is determined by the pitch for obtaining the tomograms. The greater the pitch, the smaller becomes the number, and the smaller the pitch, the greater becomes the number, on the contrary.

Further, the irradiation slice width of the X-ray beams affects image quality of the resulting tomogram. To obtain higher image quality, the slice width must be reduced.

In the X-ray CT apparatus according to the prior art, all of the bed moving speed V, the pitch P and the slice width D as the imaging conditions must be inputted from the input unit 1.

Each of these imaging conditions assume various values depending on the experience and the object of diagnosis. If such imaging conditions are set at each time for the diagnostic portions and for the object of diagnosis, quick CT measurement cannot be made in CT measurement of a large number of people such as a mass screening.

SUMMARY OF THE INVENTION

It is an object of the present invention to provide a spiral scanning type X-ray CT apparatus having high through-put. To accomplish this object, the present invention provides an interrelationship between three imaging conditions, setting of which is necessary as parameters at the time of imaging, that is, the bed moving speed, the imaging pitch of the tomogram and the slice width of the irradiation X-ray beams. The operator is required to input at least one, but not all, of these three imaging conditions, and the remaining imaging condition or conditions are automatically set in view of the interrelationship described above. Accordingly, the amount of works required for the operator for setting the imaging conditions can be reduced, and thereby through-put of the CT apparatus can be improved.

When one of these imaging conditions is fixed, the interrelationship described above remains established between the remaining two imaging conditions. The interrelationship is preferably correctable so that the experience of the operator can be reflected. At least one of the imaging conditions required for the operator to input, too, is preferably changeable.

DESCRIPTION OF THE PREFERRED EMBODIMENTS

Figure 1:
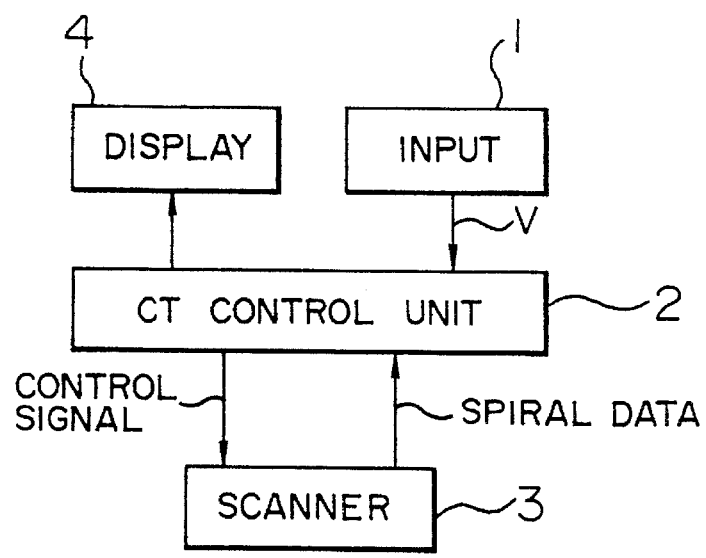
FIG. 1 shows a schematic construction of an X-ray CT apparatus according to an embodiment of the present invention.
Figure 2:
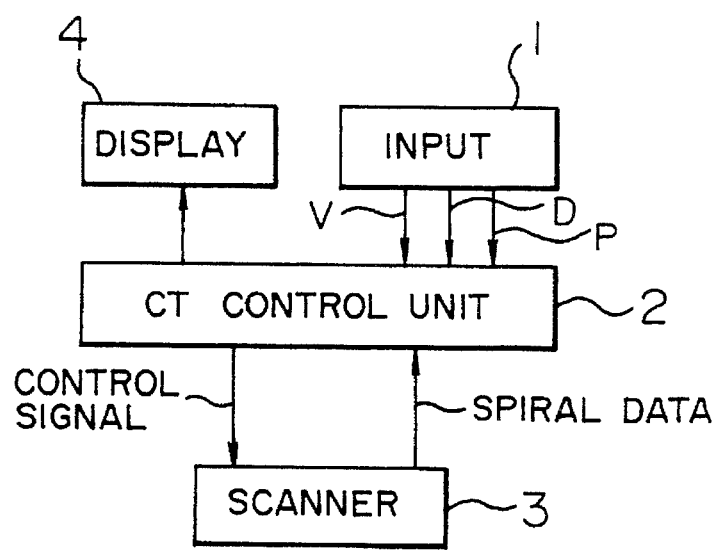
FIG. 2 shows a schematic construction of an X-ray CT apparatus according to the prior art.

FIG. 1 is a block diagram of the spiral scanning type X-ray CT apparatus according to an embodiment of the present invention. The differences of this embodiment from the CT apparatus of the prior art shown in FIG. 2 reside in the content of the output of the input unit 1 and the processing content at the CT control unit 2. In other words, the characterizing features of this embodiment reside in that only the moving speed V is given from the input unit 1, the CT control unit 2 includes a memory for storing various moving speeds and various pitches in mutual correspondence relation, the pitch P corresponding to the moving speed V from the input unit 1 is read out, and tomogram reconstruction is effected by this pitch P. Incidentally, the X-ray irradiation slice width is constant in this embodiment.

Table 1 illustrates the correspondence relation between set V and P. This table demonstrates the example where the moving speeds of 10 mm/sec, 5 mm/sec and 3 mm/sec are given to the three diagnostic portions, i.e. the chest, the liver and the head, respectively, and the pitches are 5 mm, 5 mm and 2 mm, respectively.

Table 2 illustrates an example where two kinds of moving speeds and two kinds of pitches are applied to each diagnostic portion. Which of these moving speeds is to be given is determined for each diagnostic portion, and the corresponding pitch is read out from the relationship shown in Table 2.

Definite examples of the moving speed are V=1 mm/sec, 1.5 mm/sec, 2 mm/sec, 3 mm/sec, 5 mm/sec, 10 mm/sec, 20 mm/sec, etc., inclusive of the three kinds described above.

According to this embodiment, the operator is required to input only the moving speed from outside through the input unit 1. Then, the pitch is automatically determined, and the reconstructed image can be obtained at that pitch.

TABLE 1

| moving speed (diagnostic portion) V | Pitch P |
|---|---|
| 10 mm/sec (chest) | 5 mm |
| 5 mm/sec (liver) | 5 mm |
| 3 mm/sec (head) | 2 mm |

TABLE 2

| diagnostic portion | moving speed V | pitch P |
|---|---|---|
| chest | $V_{10}$ | $P_{10}$ |
|  | $V_{11}$ | $P_{12}$ |
| liver | $V_{20}$ | $P_{20}$ |
|  | $V_{21}$ | $P_{21}$ |
| head | $V_{30}$ | $P_{30}$ |
|  | $V_{31}$ | $P_{31}$ |

Table 3 illustrates the relationship between the moving speed, the pitch and the slice width at each diagnostic portion. The example shown in Table 2 is equal to the case in this Table 3 where the slice width is kept constant.

TABLE 3

| diagnostic portion | moving speed V | pitch P | slice width D |
|---|---|---|---|
| chest | $V_{10}$ | $P_{10}$ | $D_{10}$ |
|  | $V_{11}$ | $P_{11}$ | $D_{11}$ |
| liver | $V_{20}$ | $P_{20}$ | $D_{20}$ |
|  | $V_{21}$ | $P_{21}$ | $D_{21}$ |
| head | $V_{30}$ | $P_{30}$ | $D_{30}$ |
|  | $V_{31}$ | $P_{31}$ | $D_{31}$ |

These Tables 1 to 3 are preserved in advance in the memory of the CT apparatus. The apparatus of this embodiment is constituted in such a manner that the content of each Table can be rewritten through the input unit 1.

Figure 3:
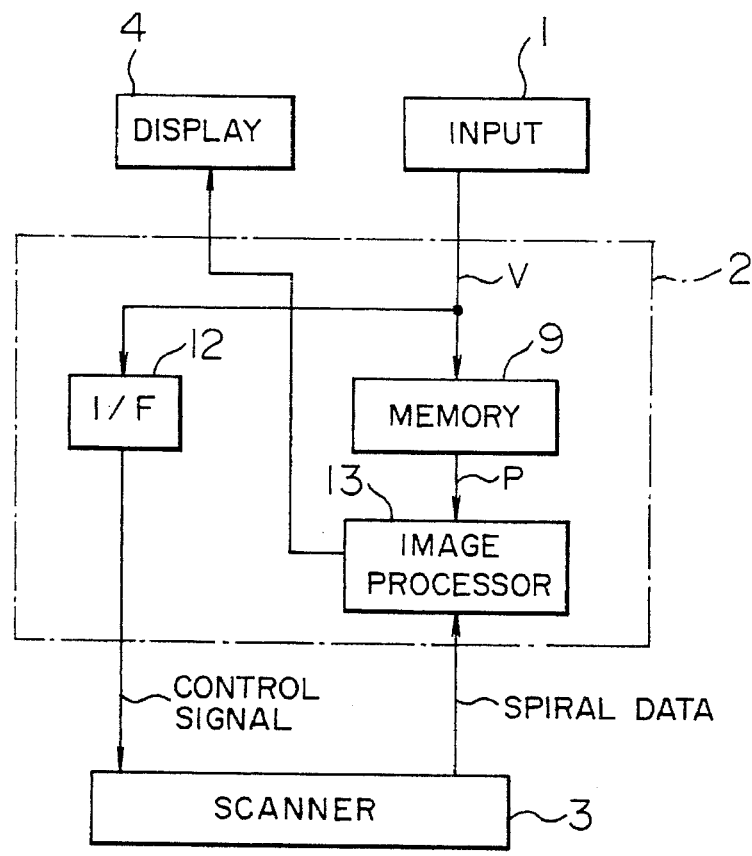
FIG. 3 shows in further detail a CT control unit of the CT apparatus shown in FIG. 1.

FIG. 3 shows the more detailed construction of the CT control unit 2. The CT control unit 2 includes a memory 9, a scanner interface 12 and an image processing unit 13. The memory 9 stores the interrelationship between the moving speed and the pitch shown in Table 1. The operator designates the diagnostic portion from the input unit 1 and inputs the bed moving speed as the imaging condition of this diagnostic portion. The signal V of the inputted moving speed is sent to the scanner 3 through the interface 12 and the bed is controlled so as to move at this moving speed. On the other hand, the signal V is applied to the V - P relationship of the memory 9, and the pitch corresponding to this signal V is stipulated. The spiral data obtained by the scanner 3 is applied to the image processing unit 13. The tomogram is reconstituted at the stipulated pitch in this image processing unit 13 by a known method, and is thereafter displayed on the display 4.

Figure 4:
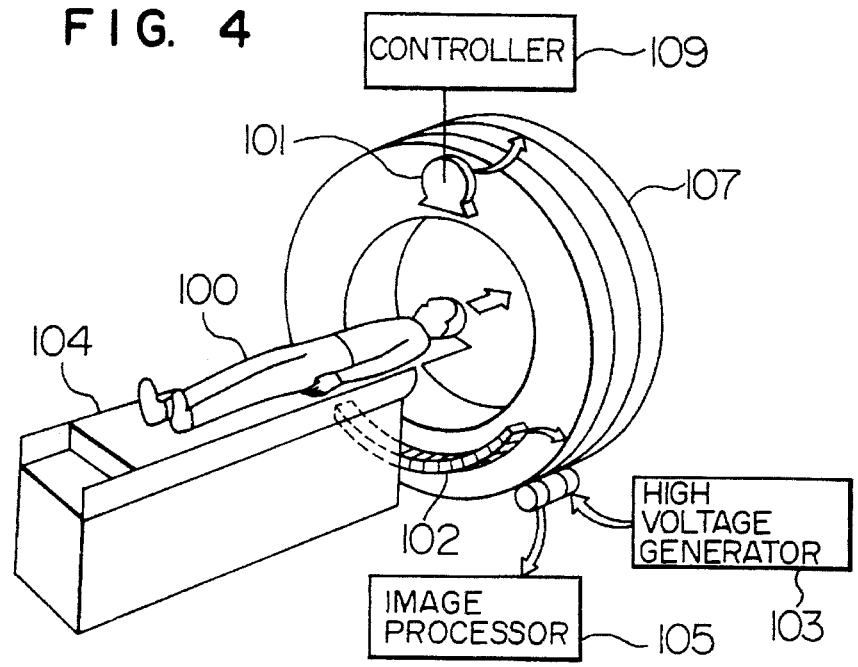
FIG. 4 shows the structure of a scanner of the embodiment shown in FIG. 1.

FIG. 4 shows the more detailed construction of the scanner. The bed 104 supporting thereon the subject 100 moves in the axial direction at the center of the annular gantry 107. The bed 104 is moved by a known mechanism, not shown in the drawing. An X-ray tube 101 and X-ray deflectors 102 are disposed inside the gantry 107 and rotate at a predetermined in a peripheral direction of the gantry 107 inside the same.

The overall construction of the spiral scanning type X-ray CT apparatus is disclosed in U.S. Pat. No. 4,789,929, and this document is herein incorporated by reference.

In the embodiment described above, the operator is required to input the bed moving speed as one of the measurement conditions. Instead, a construction which requires the operator to input the pitch of the tomogram can also be employed. In this case, the signal V corresponding to the moving speed which is stipulated in accordance with the relationship stored in the memory 9 is sent to the scanner 3. The imaging conditions which must be inputted can be changed over, whenever necessary.

On the other hand, when the relationship shown in Table 3 is stored in the memory 9, the pitch corresponding to the inputted moving speed can be stipulated and the slice width, too, can be stipulated, so that the signal corresponding to this slice width is sent to the scanner 3. Receiving this signal, the controller 109 controls the collimator (not shown) of the X-ray tube, and changes the slice width of the irradiation X-rays.

Figure 5:
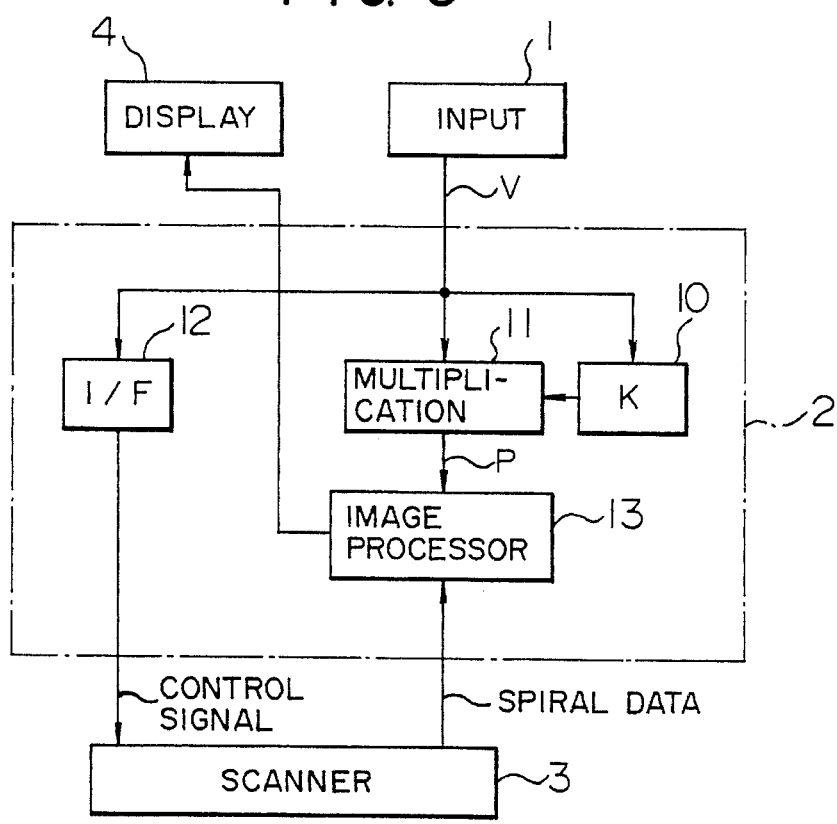
FIG. 5 shows the construction of an X-ray CT apparatus according to another embodiment of the present invention.

Another embodiment of the invention shown in FIG. 5 is different from the embodiment shown in FIG. 3 in that it has a constant memory 10 and a multiplier 11. When the moving speed V and the pitch P are assumed to satisfy the relation P=K·V, this constant K is given from the memory 10 in this embodiment. The multiplier 11 makes multiplication of K·V and obtains the pitch P. The constant K is within the range of 2≧K>0, for example, and a definite K value is determined within this range in accordance with the inspection object.

Figure 6:
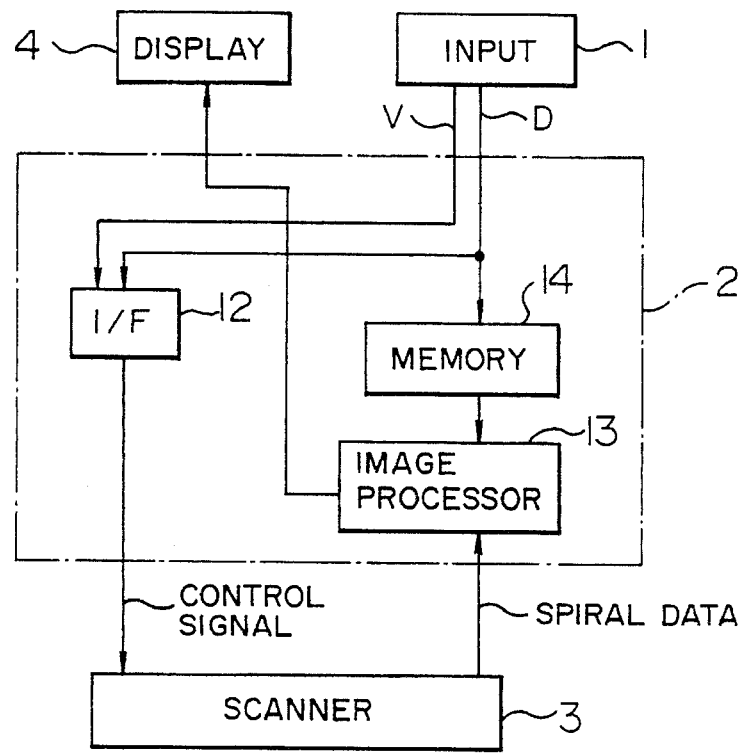
FIG. 6 shows the construction of an X-ray CT apparatus according to still another embodiment of the present invention.

FIG. 6 shows still another embodiment which automatically sets the pitch P when the slice width is variable. The term "slice width" means the width of the X-ray beams in one X-ray exposure. For instance, X-ray beams having a fan beam shape are obtained by exposure of one time, and the term "slice width" represents the width when this fan beam is viewed from the side. This slice width can be varied in various ways to compensate for the body motion, etc. The slice width can be changed by adjusting the collimator which is adjustable in the direction of the slice width. When the slice width is changed, it is changed in many cases in such a manner as to correspond to the respective pitch P.

Therefore, there is disposed a memory 14 for storing the relationship between the slice width D and the pitch P as shown in FIG. 6 so that the pitch P can be read out by the slice width D. On the other hand, the bed moving speed V and the slice width D are sent to the scanner 3 through the interface 12, and collimate control is effected so as to attain this slice width D. The bed is moved at the speed V and fan beam X-ray exposure from the X-ray source is effected. Image reconstruction is then carried out for the spiral data obtained in this way at the pitch P previously read out from the memory 14.

The present invention can improve through-put of the inspection by spiral scanning type X-ray CT, and the CT image can be computed in intervals suitable for the bed moving speed. This means uniformity of inspection. Accordingly, the present invention provides a particularly high effect in the CT inspection used for mass screening.

We claim:

1. A spiral scanning type X-ray CT apparatus comprising:
   a bed for supporting thereon a subject, said bed being moved at a moving speed determined by a first imaging condition;
   an X-ray source revolving around said bed, said X-ray source irradiating X-ray beams on said subject in a slice width determined by a second imaging condition;
   an X-ray detector revolving around said bed in synchronism with said X-ray source, for detecting said X-ray beams transmitting through said subject;
   a tomographic image formation apparatus for forming a tomogram of said subject on the basis of output signals of said X-ray detectors in a pitch of image reconstruction determined by a third imaging condition;
   a memory device for storing a predetermined relationship between said first, second and third imaging conditions;
   means for permitting input of predetermined one or two of said imaging conditions among said first, second and third imaging conditions;
   means for specifying the remaining imaging condition or conditions by referring said inputted imaging condition or conditions to said predetermined relationship; and
   means for controlling said bed, said X-ray source and said tomographic image formation apparatus on the basis of said inputted imaging condition or conditions and said specified imaging condition or conditions.

2. A spiral scanning type X-ray CT apparatus according to claim 1, wherein said input means permits input of only said first imaging condition relating to the bed moving speed, while said second imaging condition relating to the slice width of said X-ray beams is constant.

3. A spiral scanning type X-ray CT apparatus according to claim 1, wherein said input means permits input of said first imaging condition relating to said bed moving speed and said third imaging condition relating to said pitch of said image reconstruction.

4. A spiral scanning type X-ray CT apparatus according to claim 1, which further comprises:
   means for changing said predetermined relationship.

5. A spiral scanning type X-ray CT apparatus according to claim 1, which further comprises:
   means for changing said predetermined imaging condition whose input is permitted by said input means.

6. A spiral scanning type X-ray CT apparatus according to claim 1, wherein said tomographic image formation apparatus is a tomographic image reconstruction apparatus for reconstructing a tomogram of said subject.

7. A spiral scanning type X-ray CT apparatus according to claim 1, wherein said moving speed, said slice width, and said pitch have respective changeable values and are respectively determined in accordance with changeable values of said first imaging condition, second imaging condition and third imaging condition in accordance with the stored predetermined relationship between said first, second and third imaging conditions.

8. A spiral scanning type X-ray CT apparatus according to claim 7, wherein at least said moving speed has a plurality of different values, one of the different values being specified by said specifying means.

9. A spiral scanning type X-ray CT apparatus according to claim 1, wherein said input means permits input of both of said first imaging condition relating to said bed moving speed and said second imaging condition relating to said slice width, so that said third imaging condition relating to said pitch is specified by said specifying means.

10. A spiral scanning type X-ray CT apparatus according to claim 1, wherein said input means permits input of both of said second imaging condition relating to said slice width and said third imaging condition relating to said pitch, so that said first imaging condition relating to said bed moving speed is specified by said specifying means.

11. A spiral scanning type X-ray CT apparatus comprising:
   a bed for supporting thereon a subject, said bed being moved at a moving speed determined by a first imaging condition;
   an X-ray source revolving around said bed, said X-ray source irradiating an X-ray beam on said subject in a predetermined slice width;
   an X-ray detector revolving around said bed in synchronism with said X-ray source, for detecting said X-ray beams transmitting through said subject;
   a tomographic image reconstruction apparatus for reconstructing a tomogram of said subject on the basis of output signals of said X-ray detector in a pitch of image reconstruction determined by a second imaging condition;
   means for storing a predetermined relationship between said first and second imaging condition;
   means for permitting input of a predetermined one of said first and second imaging conditions;
   means for specifying the remaining imaging condition by referring said inputted imaging condition to said predetermined relationship; and
   means for controlling said bed, said X-ray source and said tomographic image reconstruction apparatus on the basis of said inputted imaging condition and said specified imaging condition with said predetermined slice width.

12. A spiral scanning type X-ray CT apparatus according to claim 11, wherein said input means only permits input of first imaging condition relating to said bed moving speed, so that said second imaging condition relating to said pitch is specified by said specifying means.

13. A spiral scanning type X-ray CT apparatus according to claim 11, wherein said input means only permits input of said second imaging condition relating to said pitch, so that said first imaging condition relating to said bed moving speed is specified by said specifying means.

14. A spiral scanning type X-ray CT apparatus according to claim 11, wherein said moving speed and said pitch have respective changeable values determined respectively by said first imaging condition and said second imaging condition in accordance with the predetermined relationship between said first and second imaging conditions.

15. A spiral scanning type X-ray CT apparatus according to claim 7, wherein at least said moving speed has a plurality of different values, one of the different values being specified by said specifying means.

* * * * *